United States Patent
Simpson et al.

(10) Patent No.: US 8,598,331 B2
(45) Date of Patent: Dec. 3, 2013

(54) CLDN5 MINI-PROMOTERS

(75) Inventors: Elizabeth M. Simpson, Vancouver (CA); Wyeth W. Wasserman, Vancouver (CA); Robert A. Holt, North Vancouver (CA); Steven J. Jones, Burnaby (CA); Daniel Goldowitz, Memphis, TN (US); Elodie Portales-Casamar, Vancouver (CA); Cletus D'Souza, Vancouver (CA); Vikramjit Chopra, Vancouver (CA)

(73) Assignee: The University of British Columbia (CA)

( * ) Notice: Subject to any disclaimer, the term of this patent is extended or adjusted under 35 U.S.C. 154(b) by 271 days.

(21) Appl. No.: 12/892,729

(22) Filed: Sep. 28, 2010

(65) Prior Publication Data

US 2011/0097803 A1    Apr. 28, 2011

Related U.S. Application Data

(60) Provisional application No. 61/272,466, filed on Sep. 28, 2009.

(51) Int. Cl.
| | |
|---|---|
| *C07H 21/02* | (2006.01) |
| *C12N 15/63* | (2006.01) |
| *C12N 5/00* | (2006.01) |
| *A01K 67/00* | (2006.01) |

(52) U.S. Cl.
USPC ........ 536/24.1; 435/455; 435/320.1; 435/325

(58) Field of Classification Search
USPC ...................... 536/24.1; 435/455, 320.1, 325
See application file for complete search history.

(56) References Cited

PUBLICATIONS

Attwood, T.K. The Babel of Bioinformatics. Science 290:471-473, 2000.*
Kyrpides et al. Whole-genome sequence annotation: "Going wrong with confidence". Mol. Microbiology 32:886-887, 1999.*
Gerhold et al. Its the genes! EST access to human genome content. BioEssays 18:973-981, 1996.*
Xie et al. Domains of the rat rDNA promoter must be aligned stereospecifically. Mol. Cel. Biol. 12:1266-1275, 1992.*
Muller et al. Repression of lac promoter as a function of distance, phase and quality of an auxiliary lac operator. J. Mol. Biol. 257:21-29, 1996.*
Alam et al. Lung surfactant protein B promoter function is dependent on the helical phasing, orientation and combinational actions of cis-DNA elements. Gene 182:103-111, 2002.*
Burek; et al., "Cloning and characterization of the murine claudin-5 promotor", Molecular and Cellular Endocrinology (2009), 298:19-24.
Chen; et al., "Brain Capillary Endothelial Cells Express MBEC1, a Protein that is Related to the *Clostridium perfringens* Enterotoxin Receptors", Laboratory Investigation (1998), 78(3):353-363.
Felinski; et al., "Glucocorticoids induce transactivation of tight junction genes occludin and claudin-5 in retinal endothelial cells via a novel cis-element", Experimental Eye Research (2008), 86:867-878.
Jasin; et al., "Targeted transgenesis", PNAS (1996), 93:8804-8808.
Matter; et al., "Holey barrier: claudins and the regulation of brain endothelial permeability", The Journal of Cell Biology (2003), 161:459-460.
Maynard; et al., "A comprehensive analysis of 22q11 gene expression in the developing an adult brain", PNAS (2003), 100(24):14433-14438.
Morita; et al., "Endothelial Claudin: Claudin-5/TMVCF Constitutes Tight Junction Strands in Endothelial Cells", The Journal of Cell Biology (1999), 147(1):185-194.
Nitta; et al., Size-selective loosening of the blood-brain barrier in claudin-5-deficient mice, The Journal of Cell Biology (2003), 161(3):653-660.
Stamatovic; et al., "Brain Endothelial Cell-Cell Junction: How to "Open" the Blood Brain Barrier", Current Neuropharmacology (2008), 6:179-192.

* cited by examiner

*Primary Examiner* — Quang Nguyen
(74) *Attorney, Agent, or Firm* — Bozicevic, Field & Francis LLP; Pamela J. Sherwood

(57) ABSTRACT

Isolated polynucleotides comprising a CLDN5 mini-promoter are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The mini-promoter may also be provided in a vector, for example in combination with an expressible sequence. The polynucleotides find use in a method of expressing a sequence of interest, e.g. for identifying or labeling cells, monitoring or tracking the expression of cells, etc.

9 Claims, 4 Drawing Sheets

CLDN5 MINI-PROMOTERS

CROSS-REFERENCE TO RELATED APPLICATIONS

Pursuant to 35 U.S.C. §119 (e), this application claims priority to the filing date of U.S. Provisional Patent Application Ser. No. 61/272,466 filed Sep. 28, 2009, the disclosure of which application is herein incorporated by reference.

FIELD OF THE INVENTION

The invention relates to gene promoters and regulatory elements. More specifically, the invention relates to CLDN5 promoter compositions and related methods.

BACKGROUND

Claudin 5 (CLDN5) a member of the claudin family. Claudins are integral membrane proteins and components of tight junction strands. Homozygous mutant neonates gradually cease movement and die within 10 hours after birth. (Nitta et al. 2003). In the adult mouse brain, CLDN5 is expressed in all major forebrain subdivisions: the neocortex, hippocampus, basal ganglia, amygdala/basal forebrain, and olfactory bulb, as well as all other CNS regions (Maynard et al. 2003). CLDN5 is expressed in cultured mouse brain embryonic cells and in freshly isolated MBEC as early as embryonic Day 7. In situ hybridization and immunocytochemical analyses revealed the presence of the CLDN5 mRNA and its protein product in brain capillary endothelial cells, as well as in a subset of other endothelial and epithelial cells (Chen et al. 1998). In the brain and lung, immunofluorescence microscopy has shown that CLDN5 is exclusively concentrated at cell-cell borders of endothelial cells of all segments of blood vessels, but not at those of epithelial cells (Morita et al. 1999). Endothelial tight junctions are an important functional part of the formation of the blood brain barrier, and CLDN5 has been shown to be a determinant of blood brain barrier permeability (Matter and Balda 2003; Nitta et al. 2003; Stamatovic et al. 2008).

Functional mouse CLDN5 promoter sequences have been identified and analyzed (Burek and Forster 2009). In this paper, the authors perform luciferase reporter assays in a brain microvascular endothelial cell line, but do not report any in vivo expression data. A 1.5 kb human CLDN5 promoter sequence was tested for expression in bovine retinal endothelial cells (Felinski et al. 2008).

Minimal human promoter elements which are capable of driving expression in specific cell types and/or in specific regions of the brain are of interest. Also of interest is the identification of minimal elements required for adequate expression and specificity that allow ease of use in expression constructs.

RELEVANT LITERATURE

References of interest include:
Burek, M. and C. Y. Forster (2009). "Cloning and characterization of the murine claudin-5 promoter." Mol Cell Endocrinol 298(1-2): 19-24;
Chen, Z., M. Zandonatti, et al. (1998). "Brain capillary endothelial cells express MBEC1, a protein that is related to the *Clostridium perfringens* enterotoxin receptors." Lab Invest 78(3): 353-63;
Felinski, E. A., A. E. Cox, et al. (2008). "Glucocorticoids induce transactivation of tight junction genes occludin and claudin-5 in retinal endothelial cells via a novel cis-element." Exp Eye Res 86(6): 867-78;
Matter, K. and M. S. Balda (2003). "Holey barrier: claudins and the regulation of brain endothelial permeability." J Cell Biol 161(3): 459-60;
Maynard, T. M., G. T. Haskell, et al. (2003). "A comprehensive analysis of 22q11 gene expression in the developing and adult brain." Proc Natl Acad Sci USA 100(24): 14433-8;
Morita, K., H. Sasaki, et al. (1999). "Endothelial claudin: claudin-5/TMVCF constitutes tight junction strands in endothelial cells." J Cell Biol 147(1): 185-94;
Nitta, T., M. Hata, et al. (2003). "Size-selective loosening of the blood-brain barrier in claudin-5-deficient mice." J Cell Biol 161(3): 653-60; and
Stamatovic, S. M., R. F. Keep, et al. (2008). "Brain endothelial cell-cell junctions: how to "open" the blood brain barrier." Curr Neuropharmacol 6(3): 179-92.

SUMMARY OF THE INVENTION

Provided herein are nucleic acid compositions and methods relating to CLDN5 promoters having a sequence other than a native CLDN5 promoter.

In one embodiment of the invention, there is provided an isolated nucleic acid fragment comprising a CLDN5 mini-promoter, wherein the CLDN5 mini-promoter comprises one or more CLDN5 regulatory elements operably linked in a non-native conformation to a CLDN5 basal promoter. In other embodiments, there is provided an isolated nucleic acid fragment comprising a CLDN5 mini-promoter, wherein the CLDN5 mini-promoter comprises a CLDN5 basal promoter. The CLDN5 mini-promoter may have a nucleic acid sequence that is substantially similar in sequence and function to SEQ ID NO: 1 or 2. The one or more CLDN5 regulatory elements may have nucleic acid sequences that are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference or antisense molecule.

In one embodiment, there is provided an expression vector comprising a CLDN5 mini-promoter element, wherein the CLDN5 mini-promoter comprises one or more CLDN5 regulatory elements operably linked in a non-native conformation to a CLDN5 basal promoter. In other embodiments, there is provided an expression vector comprising a CLDN5 mini-promoter, wherein the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. The CLDN5 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell a expression vector comprising a CLDN5 mini-promoter element, wherein the CLDN5 mini-promoter comprises one or more CLDN5 regulatory elements operably linked in a non-native conformation to a CLDN5 basal promoter. In other embodiments, there is provided a method for expressing a gene, protein, RNA interference molecule or the like in a cell, the method comprising introducing into the cell an expression vector comprising a CLDN5 mini-promoter, wherein the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. Cells of interest may include blood vessel cells in the brain. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule, or an antisense RNA molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene. In another embodiment, the CLDN5 mini-promoter element comprises a CLDN5 basal promoter element. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. In some embodiments, the cell is a blood vessel cell in the brain. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene; and 2) detecting the expression of the reporter gene in the progeny of the cell as a means of determining the lineage, identity or developmental state of the progenitor cell or progeny thereof. In other embodiments, the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. In some embodiments, the cell may be a blood vessel cell of the brain.

DETAILED DESCRIPTION

Figure 1:
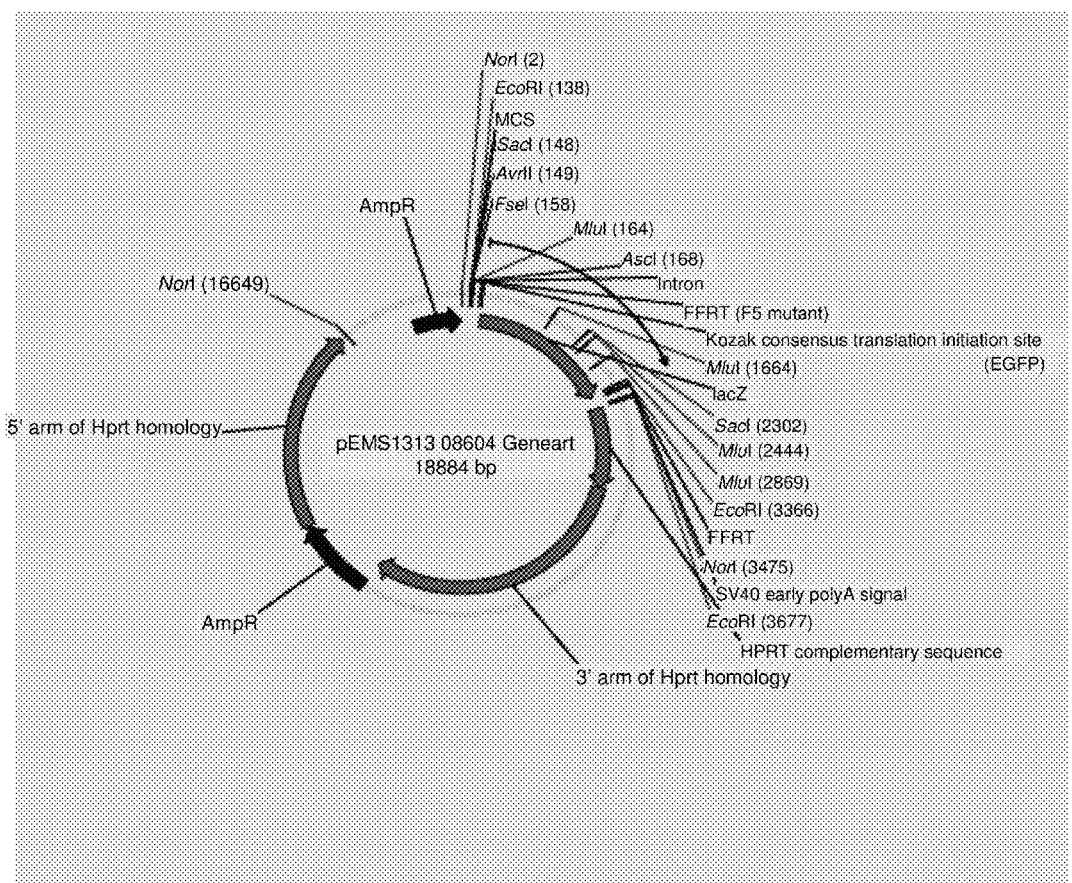
FIG. 1: Vector diagram of backbone pEMS1313

Compositions that include novel polynucleotides comprising CLDN5 promoter elements (also referred to herein as CLDN5 mini-promoters) as well as novel expression vectors comprising said CLDN5 promoter elements (or mini-promoters), are provided. Also provided are various methods utilizing the subject CLDN5 promoter (or mini-promoter) elements or expression vectors.

The term 'CLDN5' refers to the gene which encodes the CLDN5 protein, also referred to as AWAL, BEC1, CPETRL1, TMVCF, and also as MBEC1 in mouse. The human homolog of CLDN5 is encoded by the human gene identified as EntrezGene #7122, and is located at chromosomal location 22q11.21. The protein encoded by human CLDN5 has the Protein Accession #O00501.1 and/or Q53HW4 (Swiss-Prot). Other mammalian CLDN5 homologs include but are not limited to: *Rattus norvegicus* (EntrezGene #65131, Protein Accession #Q9JKD6.2), *Mus musculus* (EntrezGene #12741, Protein Accession #O54942.2).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. An 'CLDN5 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 6, and which comprises at least 1, usually at least 2, and most usually at least 4 of the identified conserved sequences listed in Table 1.

TABLE 1

List of conserved sequences in the human CLDN5 basal promoter - SEQ ID NO: 6.

| Start (relative to Ple32 sequence) | End (relative to Ple32 sequence) | Invariant sequence type |
|---|---|---|
| 346 | 522 | Conserved sequence and validated SOX18 binding site |
| 1400 | 1405 | Conserved sequence |
| 1430 | 1436 | Conserved sequence |
| 1474 | 1479 | Conserved sequence |

The start and end coordinates of the sequences are relative to the full SEQ ID NO: 6 sequence.

A promoter may also include one or more 'regulatory elements' which may also influence the expression or transcription by the promoter. Such regulatory elements encode specific DNA sequences which bind other factors, which may include but are not limited to enhancers, silencers, insulators, and/or boundary elements. An 'CLDN5 regulatory element', in the context of the present invention and as used herein, may be a nucleic acid compound having a sequence with at least 65%, at least 70%, at least 80%, at least 85%, at least 90%, at least 95%, or at least 99% similarity to SEQ ID NO: 3, 4, or 5. The present invention provides, in certain embodiments as described herein, different promoters of the CLDN5 gene. In some embodiments, the CLDN5 promoter comprises one or more CLDN5 regulatory elements operably linked to a CLDN5 basal promoter. In certain embodiments, the CLDN5 regulatory elements are directly joined with no intervening sequences. In other embodiments, the CLDN5 regulatory elements may be operably linked with intervening sequences. In general the spacing between the regulatory elements is not more than about 15 KB, generally not more than about 10 KB, usually not more than about 1 KB, more often not more than about 500 nt, and may be not more than about 100 nt, down to a direct joining of the two sequences.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene between the identified elements may be partially or completely removed. Other non-native sequences may optionally be inserted between the identified promoter elements. The term mini-promoter may also refer to a minimal promoter element in a native conformation which is capable of driving protein expression, but which has had non-essential elements removed in order to reduce its size. A mini-promoter may provide certain advantages over larger promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters would be apparent to one of skill in the art. In some embodiments of the invention, there are thus provided novel CLDN5 mini-promoters comprising one or more CLDN5 regulatory elements operably linked in a non-native conformation to a CLDN5 basal promoter. In general the spacing between the one or more CLDN5 regulatory elements and the CLDN5 basal promoter is not more than about 15 KB, generally not more than about 10 KB, usually not more than about 1 KB, more often not more than about 500 nt, and may be not more than about 100 nt, down to a direct joining of the two sequences. In other embodiments, there are provided novel CLDN5 mini-promoters comprising a CLDN5 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and/or regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which is may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

CLDN5 Promoters

The present invention herein provides novel CLDN5 mini-promoter sequences which are capable of effecting transcriptional expression in a spatial and temporal fashion which may be similar to naturally occurring CLDN5 promoters, although the invention may also provide for variation away from the native expression patterns. In some embodiments, the CLDN5 mini-promoters of the invention comprise CLDN5 promoter elements joined in a non-native configuration, thus providing advantageous characteristics. In other embodiments, the CLDN5 mini-promoters comprise basal promoters with advantageous characteristics. Also provided are novel expression vector compositions comprising CLDN5 mini-promoters which allow consistent specific spatiotemporal transcription of expression sequences. Also provided are novel methods utilizing these CLDN5 mini-promoters and expression vectors.

The CLDN5 mini-promoters of some embodiments of the invention, as described herein, comprise CLDN5 promoter elements that are joined by non-native sequences. In this context, the native intervening sequences may have been partially or completely removed, and optionally may have been replaced with non-native sequences. In such a fashion, the natural spacing of the promoter elements, for instance the human CLDN5 regulatory elements corresponding to SEQ ID NO: 3, SEQ ID NO: 4 and/or SEQ ID NO: 5 and the human CLDN5 basal promoter element corresponding to SEQ ID NO: 6, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications. The CLDN5 mini-promoters of other embodiments of the invention comprise CLDN5 basal promoters. The advantage of such basal promoters are also related to the significantly reduced size as compared to native promoters.

In certain embodiments, human CLDN5 mini-promoters having a sequences corresponding to SEQ ID NO: 1 and 2 direct expression of an expressible sequence which is operably linked downstream of the CLDN5 promoter in specific cell types in different regions of the brain (see e.g., the non-limiting working examples). The CLDN5 regulatory elements (SEQ ID NOs: 3, 4, 5) and CLDN5 basal promoter element (SEQ ID NO: 6) have sequences which are identical to those found upstream of the human CLDN5 gene.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified mini-promoter provide for a transcription rate of an expressible sequence operably linked to a modified promoter sequence that is at least about 75% the transcription rate of the promoter sequence of SEQ ID NO:1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

In one embodiment of the invention, there is provided an isolated nucleic acid fragment comprising a CLDN5 mini-promoter, wherein the CLDN5 mini-promoter comprises one or more CLDN5 regulatory elements operably linked in a non-native conformation to a CLDN5 basal promoter. In other embodiments, there is provided an isolated nucleic acid fragment comprising a CLDN5 mini-promoter, wherein the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO:

3, SEQ ID NO: 4, and/or SEQ ID NO: 5. The CLDN5 basal promoter may have a nucleic acid sequence which is substantially similar in sequence and function to SEQ ID NO: 6. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

Means of expressing a gene, protein, RNA interference molecule or the like in a cell, tissue or organ, are provided, utilizing the subject expression vectors comprising CLDN5 mini-promoters. In one embodiment, there is provided an expression vector comprising a CLDN5 mini-promoter element, wherein the CLDN5 mini-promoter comprises one or more CLDN5 regulatory elements operably linked in a non-native conformation to a CLDN5 basal promoter. In other embodiments, there is provided an expression vector comprising a CLDN5 mini-promoter, wherein the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In certain embodiments, the subject expression vectors comprising novel CLDN5 mini-promoter elements direct transcription of an expression sequence in specific cell types in specific regions of the brain and body, most notably the blood vessels in the brain. In some embodiments of the invention, there is thus provided a method for expressing a gene, protein, RNA interference molecule or the like in the targeted cells of the brain. In one embodiment, there is provided a method for expressing a gene, protein, RNA interference molecule or the like in a cell, the method comprising introducing into the cell a expression vector comprising a CLDN5 mini-promoter element, wherein the CLDN5 mini-promoter comprises one or more CLDN5 regulatory elements operably linked in a non-native conformation to a CLDN5 basal promoter. In other embodiments, there is provided a method for expressing a gene, protein, RNA interference molecule or the like in a cell, the method comprising introducing into the cell an expression vector comprising a CLDN5 mini-promoter, wherein the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. Cells of interest may include blood vessel cells in the brain. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene. In another embodiment, the CLDN5 mini-promoter element comprises a CLDN5 basal promoter element. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. In some embodiments, the cell is a blood vessel cell in the brain. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene; and 2) detecting the expression of the reporter gene in the progeny of the cell as a means of determining the lineage, identity or developmental state of the progenitor cell or progeny thereof. In other embodiments, the CLDN5 mini-promoter comprises a CLDN5 basal promoter. The CLDN5 mini-promoter may have a nucleic acid sequence which is substantially similar in sequence and function to SEQ ID NO: 1 or 2. The one or more CLDN5 regulatory elements may have nucleic acid sequences which are substantially similar in sequence and function to SEQ ID NO: 3, SEQ ID NO: 4, and/or SEQ ID NO: 5. The CLDN5 basal promoter may have a nucleic acid sequence which is substantially similar in sequence and function to SEQ ID NO: 6. In some embodiments, the cell may be a blood vessel cell of the brain.

The inventors herein further describe the present invention by way of the following non-limiting examples:

WORKING EXAMPLES

General Methods

Expression Vector

The nucleic acid fragment corresponding to SEQ ID NO: 1 or 2 was inserted into the multiple cloning site of the pEMS1313 (see FIG. 1) to produce the expression vectors used in the experiments.

Derivation of mEMS1202 Embryonic Stem Cells

Blastocysts were obtained from natural mating of B6-Hprt1$^{b-m3}$ homozygous females to 129-ROSA26 heterozygous males at 3.5 dpc. Blastocysts were flushed from uterine horns as per Hogan et al. (1994), cultured in Embryo-Max® KSOM with ½ Amino Acids, Glucose and Phenol Red (Cat #MR-121, Millipore/Chemicon, Temecula, Calif.) for 3-5 h, and then transferred onto mitomycin C (mitC; Cat#M4287, Sigma, Oakville, ON) mitotically inactivated B6-Hprt1$^{b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well developed ICM (inner cell mass) were treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON) and 0.01% β-mercaptoethanol (Sigma, Oakville, ON)) in 25%, 50%, 75% proportions (respectively) to adapt the cells to FBS containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sor$^{tm1Sor}$ and WT alleles and Hprt1$^{b-m3}$ and WT alleles. B6129F1-Gt(ROSA) 26Sor$^{tm1Sor}$/+, Hprt1$^{b-m3}$/Y (mEMS1204 series) and B6129F1-Gt(ROSA)26Sor$^{tm1Sor}$/+, Hprt1$^{b-m3}$/Y (mEMS1202 series) cell lines were identified.

Knock-in at the Hprt1 Locus

The CLDN5 expression vector plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. mEMS1202 ESCs were grown to confluence on 4-6 T75 flasks of mitC treated Hprt1$^{b-m3}$ mouse embryonic feeders (MEFs) in FBS-ESC media. ESCs (1.7–2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3$^{rd}$ day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of Knock-in Mice

Chimeric mice from targeted ESCs were generated by microinjection (Hogan et al. 1994) into E3.5 blastocysts followed by implantation into the uterine horns of 2.5 day pseudopregnant ICR females. Chimeras were identified and coat color chimerism determined as outlined below.

Male chimeras derived from the mEMS1202 cell lines were mated with B6-Alb females, and germline transmission identified by the presence of the dominant Tyr$^+$ (tyrosinase; wild type) and the A$^W$ (nonagouti; white bellied agouti) or a (nonagouti; nonagouti) alleles making the progeny appear brown with a cream belly or black, respectively. Non-germline progeny were homozygous for the recessive Tyr$^{c-2J}$ (tyrosinase; albino 2 Jackson) allele and appear white. All germline female offspring should carry the knock-in X Chromosome and were mated with B6 males. N2 offspring were analyzed for the presence of the KI allele by PCR.

Determination of Coat Color Chimerism mEMS1202-derived chimeras were identified and level of coat color chimerism determined as follows. mEMS1202 ESCs, heterozygous A$^W$/a and homozygous for the wild type Tyr$^+$ alleles will produce chimeras with agouti and black patches on a white background when injected into B6-Alb blastocysts. The agouti patches result from melanocytes derived solely from the ESCs (A$^W$/a, Tyr$^+$/Tyr$^+$), whereas 'black' patches result from melanocytes that are a mixture of ESC (A$^W$/a, Tyr$^+$/Tyr$^+$) and host (a/a, Tyr$^{c-2J}$/Tyr$^{c-2J}$). For E14TG2a injections into B6 and mEMS1202 injections into B6-Alb, overall chimerism was calculated by summing the percent of coat color patches derived solely from the ESC, plus half the percent of the ESC+host areas, where we conservatively estimated that half the melanocytes derive from the ESC and half from the host.

Reporter Gene Detection

Adult male chimeric and age matched control mice were perfused with 4% paraformaldehyde (PFA) as previously described (Young et al. 2002). Whole brains were dissected out and post-perfusion immersion fixed with PFA for 2 hours at 4° C. Brains were then transferred to 25% sucrose at 4° C. overnight with gentle shaking. The brains were cryostat sectioned sagittally at 1 mm and sections were mounted in 12-well tissue culture plates. LacZ expression was detected by using 5-bromo-4-chloro-3-indolyl β-d-galactopyranoside (x-Gal) as the substrate. The x-Gal staining solution contained the following chemicals: 1.0 mg/ml X-Gal, 2 mM potassium ferricyanide, 2 mM, potassium ferrocyanide, and 40 mM $MgCl_2$ in PBS. In brief, slide mounted brain sections are rinsed with phosphate buffered saline (PBS), then incubate with x-Gal (Boeringer Mannheim, Indianapolis, Ind.) at 37° C. from two hours to overnight. After the plates were taken out of the incubator they were rinsed with PBS and moved into PBS for storage. Bright field images were visualized on a Leica MZ125 dissecting microscope and photographed with an Olympus Coolsnap cf color camera.

Example 1

Selection of CLDN5 Promoter Elements

Under the assumption that sequences under selective pressure will be more conserved than those that are not, cross-species comparisons, or phylogenetic footprinting, were utilized to identify regulatory regions. The two mammalian species with a desirable evolutionary distance to use for this approach are human and mouse. In the specific case of CLDN5, the conservation level between human and mouse was computed taking into consideration the non-coding sequence surrounding the CLDN5 gene. For this genomic region including a lot of non-coding sequences conserved down to the frog, a threshold of 70% of identity was set up to select candidate regulatory regions. The CLDN5 basal promoter (SEQ ID NO: 6) and three upstream regulatory regions (SEQ ID NOs: 3, 4, 5) were chosen based on these criteria.

Example 2

Expression of Reporter by CLDN5 Promoter Elements

Figure 2:
FIG. 2: Expression of reporter by CLDN5 promoter elements in blood vessels in brain (Ple32)
Figure 2:
Figure 3:
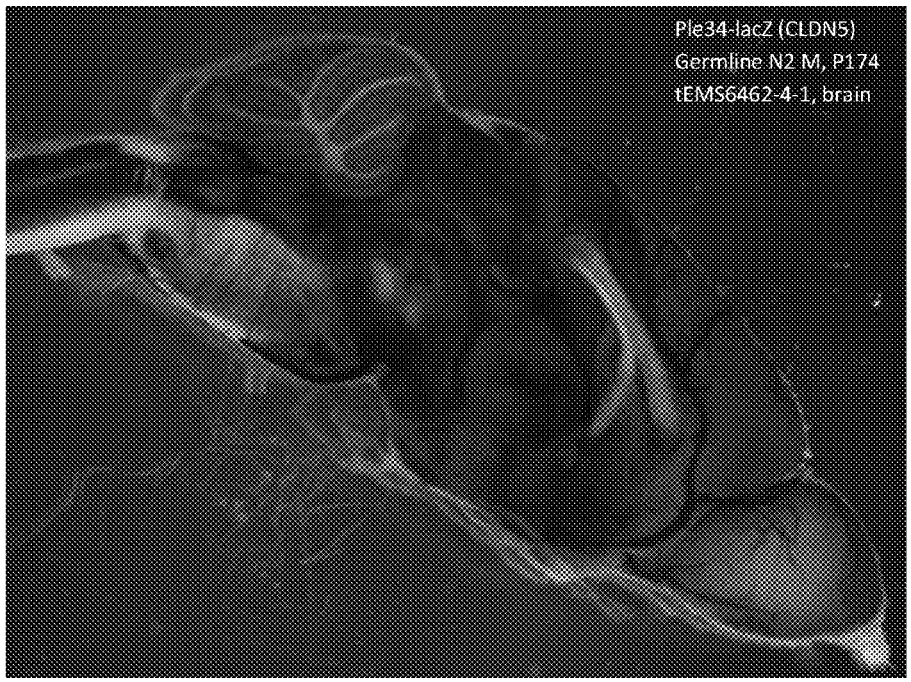
FIG. 3: Expression of reporter by CLDN5 promoter elements in blood vessels in brain (Ple34)
Figure 3:
Figure 4:
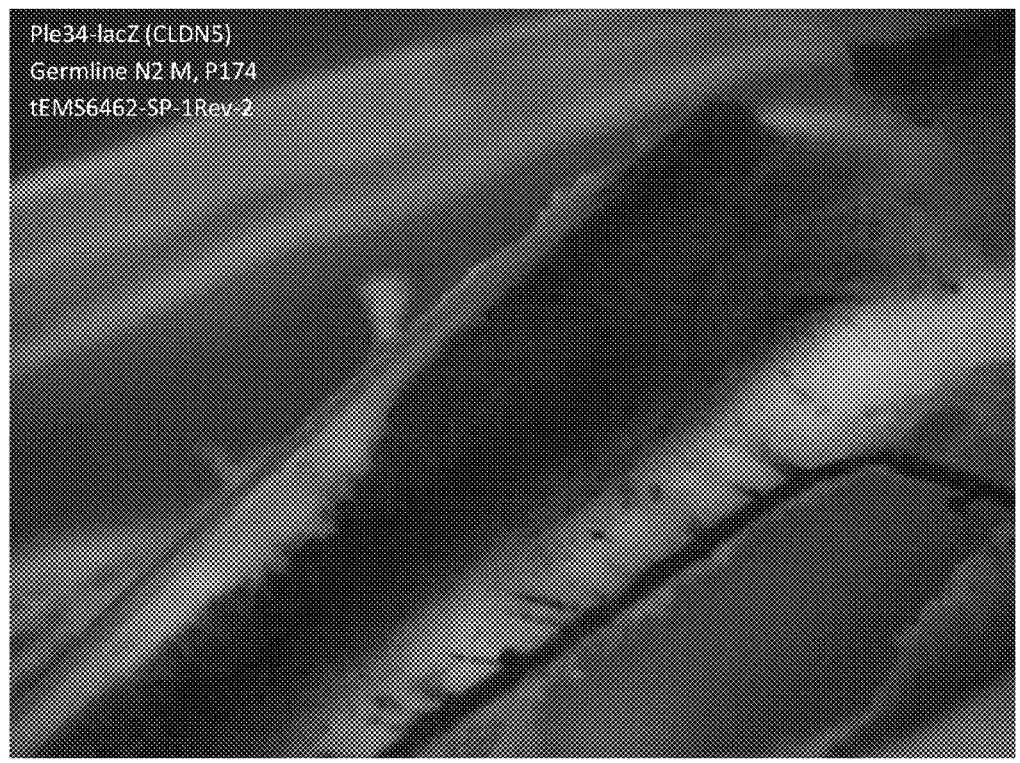
FIG. 4: Expression of reporter by CLDN5 promoter elements in spinal cord (Ple34)
Figure 4:

The CLDN5 DNA expression vectors comprising the CLDN5 promoter element corresponding to SEQ ID NO: 1 (basal promoter only) and SEQ ID NO: 2 (regulatory regions corresponding to SEQ ID NO: 3 and 4 fused to basal promoter SEQ ID NO: 6) was introduced into mouse embryonic stem cells (ESCs) at the HPRT locus. The ESCs were used to generate genetically modified mice containing CLDN5 mini-promoters. Immunohistochemical and immunofluorescence analysis of mouse brain tissue slices revealed expression in the blood vessels throughout the brain and also in spinal cord. FIG. 2 shows expression from the basal promoter (SEQ ID NO: 1) in the blood vessels of the brain. FIG. 3 shows expression from the basal promoter with two upstream regulatory regions (SEQ ID NO: 2, comprising SEQ ID NO: 3, 4 and 6 fused in non-native conformation) in the blood vessels of the brain. FIG. 4 shows expression from this same construct in spinal cord. Expression was also observed in the heart, and weak expression was observed in the liver and thymus. No expression was detected in lung.
Sequence Descriptions
SEQ ID NO: 1, human CLDN5 mini-promoter element, basal promoter only;
SEQ ID NO: 2, human CLDN5 mini-promoter–basal promoter+regulatory elements 1 and 2;
SEQ ID NO: 3, human CLDN5 regulatory element 1;
SEQ ID NO: 4, human CLDN5 regulatory element 2;
SEQ ID NO: 5, human CLDN5 regulatory element 3; and
SEQ ID NO: 6, human CLDN5 basal promoter element.

REFERENCES

Bronson, S. K., E. G. Plaehn, et al. (1996). "Single-copy transgenic mice with chosen-site integration." *Proc Natl Acad Sci USA* 93(17): 9067-72.
Burek, M. and C. Y. Forster (2009). "Cloning and characterization of the murine claudin-5 promoter." *Mol Cell Endocrinol* 298(1-2): 19-24.
Chen, Z., M. Zandonatti, et al. (1998). "Brain capillary endothelial cells express MBEC1, a protein that is related to the *Clostridium perfringens* enterotoxin receptors." *Lab Invest* 78(3): 353-63.
Cheng, J., A. Dutra, et al. (2004). "Improved generation of C57BL/6J mouse embryonic stem cells in a defined serum-free media." *Genesis* 39(2): 100-4.
Clapcote, S. J. and J. C. Roder (2005). "Simplex PCR assay for sex determination in mice." *Biotechniques* 38(5): 702, 704, 706.
Felinski, E. A., A. E. Cox, et al. (2008). "Glucocorticoids induce transactivation of tight junction genes occludin and claudin-5 in retinal endothelial cells via a novel cis-element." *Exp Eye Res* 86(6): 867-78.
Hogan, B., R. Beddington, et al. (1994). *Manipulating the mouse*. Cold Spring Harbor, Cold Spring Harbor Laboratory Press.
Hooper, M., K. Hardy, et al. (1987). "HPRT-deficient (Lesch-Nyhan) mouse embryos derived from germline colonization by cultured cells." *Nature* 326(6110): 292-5.
Jasin, M., M. E. Moynahan, et al. (1996). "Targeted transgenesis." Proc Natl Acad Sci USA 93(17): 8804-8.
Lee, K. H., C. K. Chuang, et al. (2007). "An alternative simple method for mass production of chimeric embryos by coculturing denuded embryos and embryonic stem cells in Eppendorf vials." *Theriogenology* 67(2): 228-37.
Liu, L., E. E. Geisert, et al. (2007). "A transgenic mouse class-III beta tubulin reporter using yellow fluorescent protein." *Genesis* 45(9): 560-9.
Matter, K. and M. S. Balda (2003). "Holey barrier: claudins and the regulation of brain endothelial permeability." *J Cell Biol* 161(3): 459-60.
Maynard, T. M., G. T. Haskell, et al. (2003). "A comprehensive analysis of 22q11 gene expression in the developing and adult brain." *Proc Natl Acad Sci USA* 100(24): 14433-8.
Morita, K., H. Sasaki, et al. (1999). "Endothelial claudin: claudin-5/TMVCF constitutes tight junction strands in endothelial cells." *J Cell Biol* 147(1): 185-94.
Nitta, T., M. Hata, et al. (2003). "Size-selective loosening of the blood-brain barrier in claudin-5-deficient mice." *J Cell Biol* 161(3): 653-60.
Ponchio, L., L. Duma, et al. (2000). "Mitomycin C as an alternative to irradiation to inhibit the feeder layer growth in long-term culture assays." *Cytotherapy* 2(4): 281-6.
Stamatovic, S. M., R. F. Keep, et al. (2008). "Brain endothelial cell-cell junctions: how to "open" the blood brain barrier." *Curr Neuropharmacol* 6(3): 179-92.
van der Weyden, L., D. J. Adams, et al. (2002). "Tools for targeted manipulation of the mouse genome." *Physiol Genomics* 11(3): 133-64.
Young, K. A., M. L. Berry, et al. (2002). "Fierce: a new mouse deletion of Nr2e1; violent behaviour and ocular abnormalities are background-dependent." *Behav Brain Res* 132(2): 145-58.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polynucleotide having at least 95% sequence identity to the sequence of SEQ ID NO:2.

2. The isolated polynucleotide of claim 1, operably linked to an expressible sequence.

3. A vector comprising the isolated polynucleotide of claim 1.

4. A cell comprising the vector of claim 3.

5. The cell of claim 4, wherein the vector is stably integrated into the genome of the cell.

6. The cell of claim 5, wherein the cell is a blood vessel cell or a stem cell.

7. A method of expressing a sequence of interest, the method comprising:
   (a) operably linking the sequence of interest to a polynucleotide having at least 95% sequence identity to the sequence of SEQ ID NO:2; and
   (b) introducing the polynucleotide of step (a) into a cell permissive for expression from a CLDN5 promoter.

8. An isolated polynucleotide comprising the sequence of SEQ ID NO:2.

9. An isolated polynucleotide comprising a CLDN5 regulatory element with at least 95% sequence identity to the sequence of SEQ ID NO:3, 4 or 5 operably joined to a CLDN5 basal promoter with at least 95% sequence identity to the sequence of SEQ ID NO:6, wherein the spacing between the CLDN5 regulatory element and the CLDN5 basal promoter is not more than 500 nucleotides (nt).

* * * * *

```
                             SEQUENCE LISTING

<160> NUMBER OF SEQ ID NOS: 6

<210> SEQ ID NO 1
<211> LENGTH: 1670
<212> TYPE: DNA
<213> ORGANISM: Homo Sapiens

<400> SEQUENCE: 1
cttgccttca gaacctcccc acactaggtg agccagacgc tggccttatc tcatttacca      60
tctcagagcc atctgaaggg ggagaaggga accgggcccc aggagggaga aagtcatcaa     120
acctcccaca tctgtgacca gcctcagtgc catacttttt ctatggaggg ccctgtccaa     180
tggaactgag cacagaccag ataaaagaac tgggcaccca gtggcctcag tccagggcct     240
ggagttcaaa ctttactgga aacaaggggg ccgagagaga ctggggaaag aactactaga     300
aaggggctgg tgcccccatg gggctgtggg ttttggagcc gcgtgccccc acctgagcct     360 caggggggccc ggagtgtcca caccagtgga cctttcgaga aatggctggg ccattgtgca    420
gaagaatgcc cggaaatccc gcgcctccct cctccagcaa ggatggggc tcttcctcct      480 ggccaggaaa ctccaagttg gcttccggag ggtggcctgg gggctggggt gccagggaca    540
ccatcgccac tggtgggagg gcagggcaca gcccctccgt gtccctttgt ctctcctgtc     600
tgaaggccag agcaggctgc taggcctggg gccaccactg cccctgggtg ctacacccag     660
tgtgctgggt cactgggaac ttcctgaagt ggtgtcacct gaactgggcc cccaaggatg     720
gggtgcgggc agtaccgcag gaagaggagc agcccctgtg aagattgaga ggtctgggaa     780
gcccctgcgg cttgggagag tggggtcgc caggcagggg gaaagcccct gtgccaccgc      840
tttttgccag agactcaggc tccagagagg cagtgagtgg catgggggt gaggctgggg      900 ccctgggcct gacctccaca cgcctgcctg gcctctctgt ttgccatggg atgagagaga     960
cagtgctggg actcagagcg gggctggaga gtgagagtgc gagaaagggc ctgggtgggg    1020
cttggacccc gggggcgggct ttctggagag ccccccctacg agggcctcta cggcggtgac  1080 ggggtgggg gcttctgcaa accttggtca gggaagtgga gctggctcga gtggaagaga    1140
ccacccggct cagtcgggga tgtgggagtg gactgggtgg tgcagactgg gggtcgagcg    1200
ccttctgaag tgacggggcc gggacgcgca gggaggcggc ccaagaagcg cgccctaggc    1260
cagcccagaa tgcgctcggc cgcgactagg acaacggcgg gtggggctgg gggcggctgc   1320
cgggcgggga gcggtcccgc gccctcagct accccctcaag agccgttgtt tccctaactt   1380
cagctgccag aggctctgtg attggctgcg gcacgatgac ccgcgcacgg attggctgct    1440
tcgggccggg gggccgggcc cggggggacag aatccgcccc cgaaccttca aagagggtac   1500 ccccccggcag gagctggcag acccaggagg tgcgacagac ccgcggggca aacggactgg    1560
ggccaagagc cgggagcgcg ggcgcaaagg caccagggc cgcccagggc gccgcgcagc    1620
acggccttgg gggttctgcg ggccttcggg tgcgcgtctc gcctctagcc                1670

<210> SEQ ID NO 2
<211> LENGTH: 3845
<212> TYPE: DNA
```

<213> ORGANISM: Homo Sapiens

<400> SEQUENCE: 2

```
acacagaagt atagagagaa gagtagaatg gatgcccatg tgcccagcat ccagcctcag      60
gaactaccag cctcctgctg ttttattttc tctatccatc cttcacatct ttttttttc     120
tcgttttact cacaaatact taagtatgta agtagataca cttcacccac ataatagaga    180
atactctata catgtattca tgggtcaaag gggtccctga gatacacaca attcatactc    240
atccctctga acactgcaag cgtcgtgtgg agccatttgc tttcccacac actcgctttc    300
tgccgcagca aggctggacc ctgctggagt ggtgatgtgc aggaactgcc tcatagctca    360
ggtggtaaag ttatttggct gggaactgag tctctcccca catgctgtca cacccttccc    420
ggccctgaca aacacaaaga gatgcatccc attgagtcac ccacttggct gaaccgtgta    480
cctggtaacc tccttgggag gttctttgga gggtattttt ctcctctaca caaagcatgc    540
ctgcgaagta agctgagaat gacaaaaaca ggaaagccca atcttgcaga gacagagggg    600
ccaaggcctg catgataatg cggcccaaat tcatagctca gacccaaaag aaaacaaatg    660
ttccattctt tctgtgtcca cctctaaact aagcaataca gtgagggcag taaattgcaa    720
ttacaagtaa gaactttagc agttgctgat cataaaatga aagggacaa atatgtttat     780
ccttaacagg gtcacaaata attccacagc tgttaatttt ggcagccacg actctgcagg    840
cagtatgggc tcatggtata ctatcttcat tgtcaccttg acaaagatc ctgttggcca     900
aaggcacaca ggcatcttca ggaaaactag atttaaatgg taagattaaa aaacacagtc    960
attatttaaa agcacaagaa aggtttcttt tttaaagttc actaacaaat ccagagagtg   1020
atgaccggcc tatgcttatg ttttaagct ccaaagacta ctggttctgg gaaggactgg    1080
gtcactatgt gaccttgtgt aggtctcttt tggccctgag tccaggaggg ctctgtgact   1140
ccaggttgtg gctgcgtctg gcagctaaca attgtttagt ttacagtgtc cttcctcttc   1200
atcttgtttg cattcagttg cccatgcctg cctctggggg gaggtgggaa ggaatgtggc   1260
tcctgggagg agcccagctc catgtgccat tctgaggagc caggctgcac gcccctgggc   1320
catagctgct ggtggatgga tgagtacact ggcagaggca ctgggaaggg aagacagaat   1380
tgttggccaa tagtccccctt ttactgattt tcttgtcatt tttgtgtttg ttttattata   1440
aagataacag ctgtatttga gaagaaagc tcaaactata aagaaaattt aaaattgccc    1500
tgtcttactc caactccatt ccctgaaggt ggcctgtctt aactattttt gtttctaatt   1560
cttacagtgg ttgccttcgt aattctaaag catacaaccc acatcttgat ttctcaactg   1620
tgtagtttct tttggctcta ttgtatgaaa tcaatgtgaa gttaacatat ttagacaacc   1680
tctcctcctc tcaacctctc aatttgttca ttacttttag atcttgtaat ccagtgcttt   1740
caaaatgcag gttcccaggc cgcagacaaa ctcattggaa tttgtggtgg gacctaggaa   1800
tgtgtattta taatagtctc ccctagttaa ttgtgttcac taaagtttga aaaccatcat   1860
ccttataact aaataagtgt cttaggagtt ggggcatttt tgtctgccct atcagaaacc   1920
cagctaagga aggacatcag tgaagatgga ggatgaagaa atacaaattt caccccctcca  1980
caaaaaacaa tgaaaaaagg gaaaaaactc aaaaatcaac ttttttaaaaa tagctctgga  2040
cattaaaagg cttgcagcag gccaggcatg gtggctcatg cctgttatcc cagcactttg   2100
ggaggccgag tcgggtggat tacttgagat caggagttcg agaccagcct tatagtgaaa   2160
tccagtatct actaacttgc cttcagaacc tccccacact aggtgagcca gacgctggcc   2220
ttatctcatt taccatctca gagccatctg aaggggggaga agggaaccgg gccccaggag  2280
```

-continued

```
ggagaaagtc atcaaacctc ccacatctgt gaccagcctc agtgccatac ttttctatg      2340
gagggccctg tccaatggaa ctgagcacag accagataaa agaactgggc acccagtggc     2400
ctcagtccag ggcctggagt tcaaacttta ctggaaacaa aggggccgag agagactggg     2460
gaaagaacta ctagaaaggg gctggtgccc ccatggggct gtgggttttg agccgcgtg      2520
cccccacctg agcctcaggg ggcccggagt gtccacacca gtggaccttt cgagaaatgg    2580
ctgggccatt gtgcagaaga atgcccggaa atcccgcgcc tccctcctcc agcaaggatg     2640
ggggctcttc ctcctggcca ggaaactcca agttggcttc cggagggtgg cctgggggct    2700
ggggtgccag ggacaccatc gccactgtg ggagggcagg gcacagcccc tccgtgtccc      2760
tttgtctctc ctgtctgaag gccagagcag gctgctaggc ctgggccac cactgcccct     2820
gggtgctaca cccagtgtgc tgggtcactg ggaacttcct gaagtggtgt cacctgaact    2880
ggaccccaa ggatggggtg cgggcagtac cgcaggaaga ggagcagccc ctgtgaagat      2940
tgagaggtct gggaagcccc tgcggcttgg gagagtgggg gtcgccaggc agggggaaag    3000
cccctgtgcc accgcttttt gccagagact caggctccag agaggcagtg agtggcatgg    3060
ggggtgaggc tggggccctg ggcctgacct ccacacgcct gcctggcctc tctgtttgcc    3120
atgggatgag agagacagtg ctgggactca gagcggggct ggagagtgag agtgcgagaa    3180
agggcctggg tggggcttgg accccggggc gggctttctg gagagccccc ctacgagggc    3240
ctctacggcg gtgacggggt ggggggcttc tgcaaacctt ggtcagggaa gtggagctgg    3300
ctcgagtgga agagaccacc cggctcagtc ggggatgtgg gagtggactg ggtggtgcag    3360
actgggggtc gagcgccttc tgaagtgacg gggccgggac gcgcagggag gcggcccaag    3420
aagcgcgccc taggccagcc cagaatgcgc tcggccgcga ctaggacaac ggcgggtggg    3480
gctggggcg gctgccgggc gggagcggt cccgcgccct cagctacccc tcaagagccg      3540
ttgtttccct aacttcagct gccagaggct ctgtgattgg ctgcggcacg atgacccgcg    3600
cacggattgg ctgcttcggg ccgggggggcc gggcccgggg gacagaatcc gcccccgaac    3660
cttcaaagag ggtacccccc ggcaggagct ggcagaccca ggaggtgcga cagacccgcg    3720
gggcaaacgg actggggcca agagccggga gcgcgggcgc aaaggcacca gggcccgccc    3780
agggcgccgc gcagcacggc cttgggggtt ctgcgggcct cgggtgcgc gtctcgcctc     3840
tagcc                                                                3845
```

```
<210> SEQ ID NO 3
<211> LENGTH: 1024
<212> TYPE: DNA
<213> ORGANISM: Homo Sapiens

<400> SEQUENCE: 3
acacagaagt atagagagaa gagtagaatg gatgcccatg tgcccagcat ccagcctcag     60
gaactaccag cctcctgctg ttttatttc tctatccatc cttcacatct tttttttc       120
tcgttttact cacaaatact taagtatgta agtagataca cttcacccac ataatagaga    180
atactctata catgtattca tgggtcaaag gggtccctga gatacacaca attcatactc    240
atccctctga acactgcaag cgtcgtgtgg agccatttgc tttcccacac actcgctttc    300
tgccgcagca aggctggacc ctgctggagt gtgatgtgc aggaactgcc tcatagctca     360
ggtggtaaag ttatttggct gggaactgag tctctcccca catgctgtca cacccttccc    420
ggccctgaca aacacaaaga gatgcatccc attgagtcac ccactggct gaaccgtgta     480
cctggtaacc tccttgggag gttctttgga gggtattttt ctcctctaca caaagcatgc    540
```

-continued

```
ctgcgaagta agctgagaat gacaaaaaca ggaaagccca atcttgcaga gacagagggg      600
ccaaggcctg catgataatg cggcccaaat tcatagctca gacccaaaag aaaacaaatg      660
ttccattctt tctgtgtcca cctctaaact aagcaataca gtgagggcag taaattgcaa      720
ttacaagtaa gaactttagc agttgctgat cataaaatga aagggacaa atatgtttat       780 ccttaacagg gtcacaaata attccacagc tgttaatttt ggcagccacg actctgcagg      840
cagtatgggc tcatggtata ctatcttcat tgtcaccttg acaaagatc ctgttggcca       900 aaggcacaca ggcatcttca ggaaaactag atttaaatgg taagattaaa aaacacagtc      960
attatttaaa agcacaagaa aggtttcttt tttaaagttc actaacaaat ccagagagtg     1020
atga                                                                  1024

<210> SEQ ID NO 4
<211> LENGTH: 1150
<212> TYPE: DNA
<213> ORGANISM: Homo Sapiens

<400> SEQUENCE: 4
ccggcctatg cttatgttt taagctccaa agactactgg ttctgggaag gactgggtca       60
ctatgtgacc ttgtgtaggt ctcttttggc cctgagtcca ggagggctct gtgactccag      120
gttgtggctg cgtctggcag ctaacaattg tttagtttac agtgtccttc ctcttcatct      180
tgtttgcatt cagttgccca tgcctgcctc tggggggagg tgggaaggaa tgtggctcct     240
gggaggagcc cagctccatg tgccattctg aggagccagg ctgcacgccc ctgggccata     300
gctgctggtg gatggatgag tacactggca gaggcactgg gaagggaaga cagaattgtt     360
ggccaatagt ccccttttac tgattttctt gtcattttg tgtttgtttt attataaaga       420
taacagctgt atttgagaaa gaaagctcaa actataaaga aaatttaaaa ttgccctgtc      480
ttactccaac tccattccct gaaggtggcc tgtcttaact attttttgttt ctaattctta     540 cagtggttgc cttcgtaatt ctaaagcata caacccacat cttgatttct caactgtgta     600
gtttcttttg gctctattgt atgaaatcaa tgtgaagtta acatatttag acaacctctc     660
ctcctctcaa cctctcaatt tgttcattac ttttagatct tgtaatccag tgcttttcaaa    720 atgcaggttc ccaggccgca gacaaactca ttggaatttg tggtgggacc taggaatgtg     780
tatttataat agtctccccct agttaattgt gttcactaaa gtttgaaaac catcatcctt    840
ataactaaat aagtgtctta ggagttgggg cattttgtc tgccctatca gaaacccagc      900
taaggaagga catcagtgaa gatggaggat gaagaaatac aaatttcacc cctccacaaa     960
aaacaatgaa aaagggaaa aaactcaaaa atcaacttt taaaaatagc tctggacatt       1020
aaaaggcttg cagcaggcca ggcatggtgg ctcatgcctg ttatcccagc actttgggag    1080
gccgagtcgg gtggattact tgagatcagg agttcgagac cagccttata gtgaaatcca    1140
gtatctacta                                                           1150

<210> SEQ ID NO 5
<211> LENGTH: 1155
<212> TYPE: DNA
<213> ORGANISM: Homo Sapiens

<400> SEQUENCE: 5
attgttcaac agccgcttct gggaaacttt gcagcaatct aggctctagg ctttagtcct       60
gcaaactctc ttccagggaa ctggctggcc tccggcgct gcaccccatc tgaccctccc      120
tggggttctg ctgttgcccc ctctcccatg ctggtacttt ttcctgcttt tagccaggtc      180
```

| | |
|---|---|
| tcccgtttcc cttcaccctg gtgaactcct gcttgtttgt ctaaacccat gtaagtggca | 240 |
| gctactcttc ccgacctctt agcttgccag gtaggtggct gtgtcccctc tgtcccagc | 300 |
| ccttctccat ccctgtcac ttcagtctgt ggggcctgtc ccgccaccc caggcttggt | 360 |
| ccacctgcag gtggaatgag aacgggtgag cccacggtct gcagcagcgc cttctgcact | 420 |
| gtggacattc cttccaccag cgtgtgctac aggggccagg ccagccaagg ccagtcacag | 480 |
| ggcaggacat ccccacttgt gccttttccg taaaagtgtg aagagaaagg agtgtctgaa | 540 |
| ggggtccaat gaggagagcc aagggctaga tgtgtatgcg tctgcatgcc cacgcacact | 600 |
| ccaggccctg ccagcccag aggggtgtgg gtgggcagag aggcactgca tatcctccag | 660 |
| ggtgcctggg ctgccaagag cagccccggg aagggctgca ggccctggga gagtgtcccc | 720 |
| atgccctctg tgtggtatgg tctggtcctg gatgtccagc tctggctcac ttcttgtttg | 780 |
| gacaaacgcc cacccagatc agacctgggt gccaagtcct gagggcttga caaaggcagg | 840 |
| gtgagagcca gataggatct aaggactggc tcctgggaac agtgtgggtg cccgccctgt | 900 |
| gtttacacca gcttcctgct cctgggctct ccgtctggca agctgggtgc ggccacagtc | 960 |
| tgagagggca ggaggtcgg gggccttctc ccagccctcc cgttggactc tgcacaccag | 1020 |
| tacacccagc acgtgcgctg gcaacaatg gcatgtgagc tggtagcagg tgatacatgc | 1080 |
| taaggctctg gtattgggag aatacccatt ggaatgggag gagggaaaaa cattaacctc | 1140 |
| agatattaac tttgg | 1155 |

<210> SEQ ID NO 6
<211> LENGTH: 1670
<212> TYPE: DNA
<213> ORGANISM: Homo Sapiens

<400> SEQUENCE: 6

| | |
|---|---|
| cttgccttca gaacctcccc acactaggtg agccagacgc tggccttatc tcatttacca | 60 |
| tctcagagcc atctgaaggg ggagaaggga accgggcccc aggagggaga aagtcatcaa | 120 |
| acctcccaca tctgtgacca gcctcagtgc catactttt ctatggaggg ccctgtccaa | 180 |
| tggaactgag cacagaccag ataaaagaac tgggcaccca gtggcctcag tccagggcct | 240 |
| ggagttcaaa cttactgga aacaaagggg ccgagagaga ctggggaaag aactactaga | 300 |
| aaggggctgg tgccccatg gggctgtggg ttttggagcc gcgtgccccc acctgagcct | 360 |
| caggggccc ggagtgtcca caccagtgga ccttctcgaga aatggctggg ccattgtgca | 420 |
| gaagaatgcc cggaaatccc gcgcctccct cctccagcaa ggatggggc tcttcctcct | 480 |
| ggccaggaaa ctccaagttg gcttccggag ggtggcctgg gggctggggt gccagggaca | 540 |
| ccatcgccac tggtgggagg gcagggcaca gcccctccgt gtccctttgt ctctcctgtc | 600 |
| tgaaggccag agcaggctgc taggcctggg gccaccactg cccctgggtg ctacacccag | 660 |
| tgtgctgggt cactgggaac ttcctgaagt ggtgtcacct gaactgggcc cccaaggatg | 720 |
| gggtgcgggc agtaccgcag gaagaggagc agcccctgtg aagattgaga ggtctgggaa | 780 |
| gccctgcgg cttgggagag tggggtcgc caggcagggg gaaagcccct gtgccaccgc | 840 |
| tttttgccag agactcaggc tccagagagg cagtgagtgg catggggggt gaggctgggg | 900 |
| ccctgggcct gacctccaca cgcctgcctg gcctctctgt ttgccatggg atgagagaga | 960 |
| cagtgctggg actcagagcg gggctggaga gtgagagtgc gagaaagggc ctgggtgggg | 1020 |
| cttgaccccc ggggcgggct ttctggagag ccccctacg agggcctcta cggcggtgac | 1080 |
| ggggtggggg gcttctgcaa accttggtca gggaagtgga gctggctcga gtggaagaga | 1140 |

```
ccacccggct cagtcgggga tgtgggagtg gactgggtgg tgcagactgg gggtcgagcg    1200
ccttctgaag tgacggggcc gggacgcgca gggaggcggc ccaagaagcg cgccctaggc    1260
cagcccagaa tgcgctcggc cgcgactagg acaacggcgg gtggggctgg gggcggctgc    1320
cgggcgggga gcggtcccgc gccctcagct accctcaag agccgttgtt tccctaactt    1380
cagctgccag aggctctgtg attggctgcg gcacgatgac ccgcgcacgg attggctgct    1440
tcgggccggg gggccgggcc cggggacag aatccgcccc cgaaccttca aagagggtac    1500
cccccggcag gagctggcag acccaggagg tgcgacagac ccgcggggca aacggactgg    1560
ggccaagagc cgggagcgcg ggcgcaaagg caccagggcc cgcccagggc gccgcgcagc    1620
acggccttgg gggttctgcg ggccttcggg tgcgcgtctc gcctctagcc               1670
```